United States Patent [19]

Abel

[11] Patent Number: 5,576,457
[45] Date of Patent: Nov. 19, 1996

[54] CATALYST AND PROCEDURE FOR PREPARATION OF VINYL ACETATE

[75] Inventor: Roland Abel, Oberhausen, Germany

[73] Assignee: Hoechst Celanese Corporation, North Somerville, N.J.

[21] Appl. No.: 448,146

[22] Filed: May 23, 1995

[51] Int. Cl.$^6$ .................................................. C07C 67/05
[52] U.S. Cl. ........................................... 560/245; 502/326
[58] Field of Search ............................................. 560/245

[56] References Cited

U.S. PATENT DOCUMENTS

| | | | |
|---|---|---|---|
| 3,346,624 | 10/1967 | Schaeffer et al. | 260/497 |
| 3,346,626 | 10/1967 | Schaeffer et al. | 260/497 |
| 3,373,189 | 3/1968 | Lum et al. | 260/497 |
| 3,471,532 | 10/1969 | Young | 260/410.9 |
| 3,557,192 | 1/1971 | Hillman | 260/497 |
| 3,579,569 | 5/1971 | Montgomery et al. | 260/497 |
| 3,622,620 | 11/1971 | Horiie et al. | 260/497 A |
| 3,650,986 | 3/1972 | Sennewald et al. | 252/431 C |
| 3,655,747 | 4/1972 | Sennewald et al. | 260/530 R |
| 3,743,607 | 7/1973 | Sennewald et al. | 252/430 |
| 3,758,551 | 9/1973 | Murib et al. | 260/486 R |
| 3,761,513 | 9/1973 | Sennewald et al. | 260/497 A |
| 3,775,342 | 11/1973 | Kronig et al. | 252/430 |
| 3,822,308 | 7/1974 | Kronig et al. | 260/497 A |
| 3,939,199 | 2/1976 | Fernholz et al. | 260/469 |
| 3,946,068 | 3/1976 | Calcagno et al. | 260/497 A |
| 3,970,697 | 7/1976 | Scheben et al. | 260/533 R |
| 4,048,096 | 9/1977 | Bissot | 252/430 |
| 4,057,575 | 11/1917 | Klass | 560/245 |
| 4,119,567 | 10/1978 | Bartsch | 252/430 |
| 4,133,962 | 1/1979 | Fernholz et al. | 560/245 |
| 4,490,481 | 12/1984 | Boitiaux | 502/330 |
| 4,533,779 | 8/1985 | Boitiaux et al. | 585/259 |
| 4,902,823 | 2/1990 | Wunder et al. | 560/245 |
| 5,194,417 | 3/1993 | Smith | 502/330 |

FOREIGN PATENT DOCUMENTS

| | | |
|---|---|---|
| 948211 | 5/1974 | Canada. |
| 68/1437 | 3/1968 | South Africa. |
| 68/2015 | 3/1968 | South Africa. |
| 69/5822 | 8/1969 | South Africa. |
| 976613 | 12/1964 | United Kingdom. |
| 1067850 | 5/1967 | United Kingdom. |
| 1086347 | 10/1967 | United Kingdom. |
| 1116588 | 6/1968 | United Kingdom. |
| 1154517 | 6/1969 | United Kingdom. |
| 1209125 | 10/1970 | United Kingdom. |
| 1216499 | 12/1970 | United Kingdom. |
| 1216500 | 12/1970 | United Kingdom. |
| 1283737 | 8/1972 | United Kingdom. |
| 1511869 | 5/1978 | United Kingdom. |
| 1521652 | 8/1978 | United Kingdom. |
| 1559540 | 1/1980 | United Kingdom. |
| 1571910 | 7/1980 | United Kingdom. |

OTHER PUBLICATIONS

"Selectivity Problems & Kinetic Models in the Palladium Catalysed Oxidation of Ethene & Acetic Acid to Ethenyl Acetate Related Reactions of Propene, 1–Butene and 1–Hexene", Davidson, J. M., Mitchell, P. C., Raghavan, N. S., Proceedings of the International Chemical Reaction Conference, pp. 300–313 (1989).

"The Mechanism of the Palladium–Catalyzed Synthesis of Vinyl Acetate from Ethylene in a Heterogeneous Gas Reaction", Nakamura, S., Yasui, T., Journal of Catalysis, 17, pp. 366–374 (1970).

"Production of Vinyl Acetate by Acetoxidation of Ethylene", Shetty, R. S., Kashyap, D. H., Chandalia, S. B. Indian Journal of Technology, vol. 11 1973, pp. 170–173.

"Make Vinyl Acetate Via Ethylene", Schwerdtel, W., Hydrocarbon Processing, Petrochemical Guide, pp. 187–191, vol. 47 #11, (1968).

"Vinyl Acetate: how, where, who–future", Stobaugh, R. B., Allen, Jr. W. C., Sternberg, V. R. H., Hydrocarbon Processing, Petrochemical Guide, Part 18, pp. 153–161, May 1992.

"Manufacture of Vinyl Acetate from Ethylene", Shetty, R. S., Chandalia, S. B., Chemical Processing & Engineering, Sep. 1969.

"The Mechanism of Vinyl Acetate Formation by Gas–Phase Catalytic Ethylene Acetoxidation", Samanos, B, Boutry, P., Montarnal, R. Journal of Catalysis 23, pp. 19–30 (1971).

"Catalytic Activity of Supported Liquid–Phase Lithium–Palladium Acetate Catalysts in the Oxidation of Ethylene to Vinyl Acetate", Zaidi, S. A. H., Applied Catalysis, 38 (1988) pp. 353–358.

"Wacker Oxidation Catalysis in a Supported Aqueous Phase", Arhancet, J. P., Davis, M. E., Hanson, B. E., Catalysis Letters 11, Sep. 1991, pp. 129–136.

Vinyl Polymers (Acetate), Kirk Othmer Encyclopedia of Chemical Technology, 3rd Edition, vol. 23, pp. 817–825, J. Wiley & Sons (1983).

"Chemistry of Catalytic Processes, " Gates, B. C., Katzer, Schuit, G. C. A., pp. 137–140 (1979).

"Ethylene and Its Derivatives", Edited by Miller, S. A., Chapter 12, pp. 942–956 (1974).

Primary Examiner—Michael L. Shippen
Attorney, Agent, or Firm—Donald R. Cassady; M. Susan Spiering

[57] ABSTRACT

A catalyst useful for the manufacture of vinyl acetate from acetic acid, oxygen and ethylene which contains palladium, calcium, and at least one of zirconium and rhenium and the method of manufacture of vinyl acetate using the catalyst.

5 Claims, No Drawings

CATALYST AND PROCEDURE FOR PREPARATION OF VINYL ACETATE

BACKGROUND OF THE INVENTION

It is known that ethylene can be reacted with acetic acid and oxygen or oxygen-containing gases in the vapor phase on a palladium/cadmium/akali-metal containing catalyst bed to produce vinyl acetate. A space-time yield of over 200 grams per liter hour is obtained (U.S. Pat. Nos. 3,939,199; 4,668,819; 4,902,823; 5,225,388; European Patent Publications A-0 403 950, A-0 565 952, A-0 634 208, A-0 634 209, and A-0 634 214).

SUMMARY OF THE INVENTION

One object of the invention is a procedure for the preparation of vinyl acetate in the gas phase from ethylene, acetic acid and oxygen or oxygen-containing gases on a catalyst which contains palladium and/or its compounds, cadmium compounds as well as alkali metal compounds, on a support characterized by the catalyst containing at least a rhenium and/or at least one zirconium compound.

A further object of the invention is a catalyst which contains palladium and/or its compounds, cadmium compounds and as alkali metal compounds, on a support which additionally contains at least one rhenium and/or at least one zirconium compound.

Surprisingly, it has now been found that by the addition of at least one rhenium and/or at least one zirconium compound, such catalysts can be significantly improved, i.e., they produce a higher space-time yield of vinyl acetate with the same or higher selectivity and with slower deactivation.

DETAILED DESCRIPTION OF THE INVENTION

Suitable supports for the catalyst of the present invention are the known supports such as silica, aluminum oxide, aluminosilicates, silicates, titanium oxide, zirconium oxide, titanates, silicon carbide and carbon. Particularly suitable are supports of this kind with a specific surface area of 40 to 350 $m^2/g$ (measured by the BET method) and with an average pore size of 50 to 2000 Å (as measured by mercury porosimetry), above all silicic acid ($SiO_2$) and $SiO_2$—$Al_2O_3$ mixtures. These supports are used in the form of spheres, tablets, rings, stars and other shapes whose diameter or length and width is usually 3 to 9 mm.

Total pore volume of the support is preferably 0.4–1.2 ml/g of which less than 10% of the volume consists of "micropores" with a pore diameter below 30 Å (Angstrom). Such supports can be prepared from aerogenic $SiO_2$ or an aerogenic $SiO_2$—$Al_2O_3$ mixture present in the form of glassy microspheres which can be prepared, for example, by flame hydrolysis of silicon tetrachloride or silicon tetrachloride-aluminum trichloride mixtures in an oxyhydrogen flame (U.S. Pat. No. 3,939,199). These mixtures are available commercially under the names Aerosil® or Cabosil®.

Particularly preferred is the use of supports pressed with the aid of organic fillers from microspheres of $SiO_2$ or $SiO_2$—$Al_2O_3$ mixtures with a surface area of 60–250 $m^2/g$ and a pore volume of 0.4 to 1.2 ml/g (European Patent Publication-A-0 403 950). The particles of this support have a grain size of 4 to 9 mm, with 5 to 90% of the pore volume consisting of pores with 200 to 3000 Å radii and 50 to 90% pores of 70 to 100 Å radii. It is particularly preferred when these support particles are pressed with addition of one or several $C_2$–$C_{20}$ carboxylates of Li, Mg, Al, Zn, Fe, or Mn as binders and with addition of organic fillers (such as sugar, urea, higher fatty acids, long-chain paraffins, micro-crystalline cellulose) and lubricants (such as kaolin, graphite, metallic soaps) to produce tablets by extrusion (U.S. Pat. No. 5,225,388). Following the preceding, the particles are calcined for 0.25–5 hours at 500°–900° C. in $O_2$-containing gases.

The catalytically active substances can be added to the support in the usual fashion, for example by a single or multiple soaking with a solution of the active substances, followed by drying and subsequent reduction. However, the active substances can also be added by single or multiple spraying, evaporation or immersion or by precipitation on the support.

Solvents for the catalytically active substances are, above all, water or unsubstituted 2 to 10-carbon fatty acids, such as acetic acid, propionic acid, n- and iso-butyric acid and the various valeric acids. Because of physical properties and price, acetic acid is the preferred carboxylic acid. Use of an additional inert solvent is helpful when the substances used are not soluble enough in the carboxylic acid employed. Thus. e.g., palladium chloride is considerably more soluble in aqueous acetic acid than in glacial. Additional solvents are those which are inert and miscible with the carboxylic acid, for example water or an ether such as tetrahydrofuran or dioxan, but also hydrocarbons such as benzene.

It is possible to prepare so called catalysts "impregnated throughout", in which the catalytically active metal compound has penetrated to the core of the support particle as well as so called "shell catalysts" in which the metal salts have not reached the core but only a more or less thick outer part of the support particle, i.e. the so-called shell of the particle. In both cases the added elements can be used as solutions of their compounds added either singly or in any desired combination. Preferably used are solutions which contain at least one compound of the element to be applied.

Particularly preferred is the use of a single solution containing precisely one compound of each of the elements to be applied. Hereinafter by "the solution" is meant to be one containing at least one compound of one of the elements Pd, alkali metal, Cd, Re, Zr, or a solution containing at least one compound of two or more elements.

The preferred procedure for preparation of catalysts impregnated throughout is as follows (U.S. Pat. Nos. 4,902, 823, 3,393,190, and 4,668,819):

Impregnation of the catalyst support with the solution of the active components is performed by covering the support with the solution, then pouring or filtering off the excess solution. To prevent solvent losses it is advisable to employ only an amount of solution corresponding to the integral pore volume of the catalyst support and mixing carefully to wet the support particles uniformly. It is useful to perform impregnation and mixing concurrently, for example in a rotary drum or a tumbler drier, followed immediately by drying. Further, it is generally useful to formulate the composition of the solution for impregnation of the support in such a way as to incorporate the desired amount of active materials in a single impregnation. However, it is possible to add this amount by several impregnations, preferably with drying after each impregnation.

Shell catalysts are preferably prepared by one of the three methods listed below, always using a solution of at least one compound of one of the elements Pd, alkali metal, Cd, Re and/or Zr with a dynamic viscosity of at least 0.003 Pa*s.

1. While thoroughly mixing, the support particles are sprayed once or several times with the solution in the form of droplets of an average diameter of at least 0.3 mm, or in the form of liquid streams and dried immediately after each spraying. "Immediate" drying means that drying must follow spraying without interruption. It is generally adequate if drying of the particles begins at the latest 30 minutes after spraying. The volume of the solution for each spraying is 5 to 80% of the pore volume of the support particles. This method is described in detail in European Patent Publication A-0 634 214, which is here specifically incorporated by reference.

2. While thoroughly mixing, the support particles are soaked once or repeatedly with the solution and dried immediately after each soaking. "Immediately" has here the same meaning as in method 1, and the volume of solution for each soaking is 5 to 80% of the pore volume of the support particles. This method is described in detail in European Patent Publication A-0 634 209, which is here incorporated by reference.

3. While thoroughly mixing, the support particles are soaked once or repeatedly and dried after each soaking but, in contrast to method 2, the volume of solution does not have an upper limit: it now exceeds 80% of the pore volume. As a result of the larger volume, thorough mixing is not a requisite but in general is useful. However, the duration of each soaking and the time lapse to begin the follow-up drying must be so brief that after each drying the catalytically active elements from the preceding are located in a shell comprising 5 to 80% of the pore volume of the particles. The briefness of this time lapse can be easily ascertained by preliminary tests. This method is described in detail in European Patent Publication A-0 634 208, which is here incorporated by reference.

A suitable method for determination of the obtained shell thickness consists of cutting open a representative number of impregnated and dried support particles and measuring the shell thickness under a microscope. Preferably fewer than 5% of the particles should have a shell thickness that deviates from the desired value by more than 15%.

Drying of the soaked or sprayed catalyst support is preferably performed under reduced pressure (o.i to 0.8 bar) for both impregnated-throughout and shell catalysts. Drying temperature generally should be 50° to 80° C., preferably 50° to 70° C. Further, it generally is recommended to perform drying in an inert gas stream, for example a nitrogen or carbon dioxide stream. Residual solvent content after drying should be preferably less than 8 wt %, particularly less than 6 wt %.

Finished catalysts should contain the following amounts of the catalytically active elements:

Palladium content is generally 0.6 to 3.5 wt %, preferably 0.8 to 3.0 wt %, particularly 1.0 to 2.5 wt %. Alkali element content is generally 0.3 to 10 wt %. Potassium is preferably used, generally at 0.5 to 4.0 wt %, 30 preferably at 1.0 to 3.0 wt %, particularly at 1.5 to 2.5 wt %. Cadmium content is generally 0.1 to 2.5 wt %, preferably 0.4 to 2.5 wt %, particularly 1.3 to 2 wt %. Rhenium and zirconium contents are generally 0.05 to 3 wt %, preferably 0.05 to 1 wt %, particularly 0.05 to 0.5 wt %. Rhenium and zirconium may also be present jointly in the catalyst, and in this case the total content of both elements falls inside the above ranges.

The indicated percentages refer always to the amounts of elements Pd, alkali element, Cd, Zr and/or Re, relative to the total mass of the catalyst (active elements plus anions plus support material).

Appropriate compounds for application to the support are all compounds of palladium, cadmium, alkali metal, rhenium and zirconium that are soluble and do not contain components poisonous to the catalyst, as e.g. sulfur: preferred are acetates and chlorides. In the case of chlorides it must be ensured that they are removed before use of the catalyst for synthesis of vinyl acetate. This is accomplished by washing the doped support, e.g. with water, after the palladium added as chloride had been converted to an insoluble form, as by reduction or precipitation with hydroxides.

Particularly suitable palladium compounds are its carboxylates, preferably its salts with 2 to 5 carbon aliphatic monocarboxylic acids, such as acetate, propionate, or butyrate. Also suitable, for example, are nitrate, nitrite, hydroxide, oxalate, acetylacetonate, acetoacetate. Palladium acetate is a particularly preferred palladium compound due to its good solubility and availability.

The alkali metal compound is preferably at least one K, Rb or Cs compound, particularly at least one K compound. Above all, suitable compounds are carboxylates, particularly acetate and propionate. Also suitable are also compounds which under the reaction conditions, become converted to acetate, for example hydroxide, oxide or carbonate. The most appropriate cadmium compound is acetate. Suitable zirconium compounds are acetate and acetylacetonate. Most suitable rhenium compounds are $Re_2O_7$ and $(NH_4)ReO_4$.

If reduction of the palladium compound is to be performed, which is sometimes useful, it can be done with a gaseous reducing agent, for example hydrogen, methanol, formaldehyde, ethylene, propylene, isobutylene, butylene and other olefines. Reduction temperature is generally between 40° and 260° C., preferably between 70° and 200° C. Generally it is convenient to use a reducing agent diluted with inert gas containing 0.01 to 50 vol %, preferably 0.5 to 20 vol % reducing agent. Inert gases for example, can be nitrogen, carbon dioxide or a noble gas. The amount of reducing agent is based on the amount of palladium: the reduction equivalent should be at least 1 to 1.5 times the oxidation equivalent but larger amounts of reducing agent are of no concern. Reduction is performed following drying.

Vinyl acetate is prepared by passing acetic acid, ethylene and oxygen or oxygen-containing gases over the finished catalyst at temperatures of 100° to 220° C., preferably 120° to 200° C. and pressures of 1 to 25 bar, preferably 1 to 20 bar with the unreacted components optionally recirculated. Concentration of oxygen is suitably kept below 10 vol % (based on the acetic acid free gas mixture). However, a dilution with inert gases such as nitrogen is sometimes advantageous. Carbon dioxide is particularly appropriate for dilution of the recycle gas as it is formed in small amounts in the course of the reaction.

The catalysts according to the invention allow attaining a higher space-time yield and the same or higher selectivity at longer operating times than with catalysts which do not contain rhenium or zirconium.

The following examples will illustrate the invention. The percentages given for the elements Pd, Cd, Zr, Re and K are weight percentages relative to total catalyst mass.

The catalyst support used was $SiO_2$ in the form of tablets with a diameter and height of 6 mm. The tablets were pressed from ®Aerosil powder with magnesium stearate as binder according to U.S. Pat. No. 5,225,388. Surface area of the support was 120 $m^2/g$, its pore volume 0.784 ml/g and its bulk density 500 g/l. Pore volume of one liter of support was 392.

I. Catalysts impregnated throughout

COMPARISON EXAMPLE 1

1l silica of support was soaked with a solution of 24.3 g palladium acetate, 21.3 g cadmium acetate and 23.8 g potassium acetate in 392 ml glacial acetic acid (solution volume=100% of support pore volume). It was then dried under nitrogen in a drying cabinet at 200 mbar to a residual acetic acid content of 6 wt %: drying temperature was 65° C. The finished catalyst contained 2.3 wt % Pd, 1.8 wt % Cd and 1.9 wt % K. It was impregnated throughout, i.e. to its core. 50 g of this catalyst was placed in a reaction tube of 8 mm inside diameter and 1.5 m length. The gas to be reacted was then passed for several days over the catalyst at a pressure of 8 bar (reactor inlet) and a catalyst temperature of 150° C. The gas consisted of 27 vol % ethylene, 59 vol % nitrogen, 12 vol % acetic acid and 6 vol % oxygen. Results can be seen in Table 1, where "relative rate of output loss" is the ratio of output loss (=initial output of the test minus end output of the test) over test duration relative to the ratio for the catalyst of example 1. This catalyst has a ratio (=relative rate of output loss) of 1.

Example 1a

It was proceeded as in Example 1, with the exception that the solution also contained 7.5 g zirconium acetylacetonate and the acetic acid used was 389 ml. Results are in Table 1.

Example 1b 1l of the catalyst of comparison example 1 was soaked at room temperature with a solution of 4.2 g $Re_2O_7$ in 308 ml water (solution volume=100% of catalyst pore volume). It was then dried as in example 1 to a final water content of 6 wt %. Testing was as in example 1. Results are shown in Table 1.

TABLE 1

| (catalyst impregnated throughout) | | | |
|---|---|---|---|
| | output* (g/lh) | selectivity (%) | relative rate of output drop |
| comparison example | 813 | 94.3 | 1 |
| example 1a | 870 | 94.5 | 0.7 |
| example 1b | 840 | 94.8 | 0.7 |

*initial output (grams of vinyl acetate per liter catalyst and hour)

II Shell catalysts

COMPARISON EXAMPLE 2

25.3 g palladium acetate, 25 g cadmium acetate and 25.3 g potassium acetate were dissolved at 65° C. in 130.0 ml water-free acetic acid (glacial acetic acid) (solution volume= 33% of pore volume) and the highly viscous solution (7 mPa*s) placed in a preheated vessel. One liter catalyst support was also heated to 65° C. and placed in a round-bottomed flask. The entire impregnation solution was then poured on the support particles and the mixture thoroughly mixed until the solution had been totally absorbed by the particles. This procedure took 3 minutes.

Drying as in example 1 followed. The finished catalyst contained 2.3 wt % Pd, 1.8 wt % Cd and 1.9 wt % K. Thickness of the shell was 0.8 mm.

Testing was as in comparison example 1. Results can be seen in Table 2. "Relative rate of output drop" is defined as for comparison example 1, i.e. also relative to the catalyst used there.

Example 2a

The procedure was as in comparison example 2 except that the solution contained an additional 7.0 g zirconium acetyl-acetonate. Shell thickness was 0.8 mm. Results are shown in Table 2.

Example 2b 1l of catalyst prepared as in example 2 was soaked at room temperature with a solution of 3.5 g $Re_2O_7$ in 300 ml water (solution volume=100% of catalyst pore volume). It was then dried as in comparison example 1 to a water content of 6 wt %. Testing was as in comparison example 1. Results are shown in Table 2.

TABLE 2

| (shell catalysts) | | | |
|---|---|---|---|
| | output* (g/lh) | selectivity (%) | relative rate of output drop |
| Comparison example 2 | 922 | 95.8 | 1.4 |
| example 2a | 950 | 96.1 | 0.9 |
| example 2b | 940 | 96.0 | 1.0 |

*initial output (grams vinyl acetate per liter catalyst and hour)

What is claimed is:

1. In the process for preparation of vinyl acetate in the vapor phase comprising reacting ethylene, acetic acid and oxygen or oxygen-containing gases in the presence of a catalyst containing palladium and/or its compounds, cadmium, and alkali metal compounds on a support, the improvement comprising using a catalyst that additionally contains at least a rhenium and/or a zirconium compound.

2. The process according to claim 1 wherein the catalyst contains at least a potassium compound.

3. The process according to claims 1 or 2 wherein the catalyst contains 0.05 wt % to 3 wt % rhenium and/or zirconium relative to total mass of catalyst.

4. The process according to claims 1, 2, or 3 wherein the catalyst contains 0.05 wt % to 1 wt % rhenium and/or zirconium relative to total mass of catalyst.

5. The process according to claims 1, 2, 3, or 4 wherein the catalyst contains 0.05 wt % to 0.5 wt % rhenium and/or zirconium relative to total mass of catalyst.

* * * * *

UNITED STATES PATENT AND TRADEMARK OFFICE
CERTIFICATE OF CORRECTION

PATENT NO.   : 5,576,457
DATED        : 11/19/1996
INVENTOR(S)  : ABEL

It is certified that error appears in the above-identified patent and that said Letters Patent is hereby corrected as shown below:

Column 1, line 58: "mixtures" should read "microspheres".
Column 1, line 67: before "pores" there should be included "of the pore volume consisting of".
Column 2, line 38: "of the element" should read "of each of the elements".
Column 3, line 42: "0.i" should read "0.1".
Column 3, line 55: "30" should be deleted.
Column 4, line 66: "392" should read "392 ml".
Column 5, line 12: "50 g" should read "50 ml".
Column 5, line 22: "of example 1" should read "of comparison example 1".
Column 5, line 31: "catalyst of" should read "catalyst as prepared in".
Column 5, line 36: "in example 1" should read "of comparison example 1".
Column 6, line 21: "in example 2" should read "of comparison example 2".

Signed and Sealed this

Eighth Day of July, 1997

*Attest:*

BRUCE LEHMAN

*Attesting Officer*     Commissioner of Patents and Trademarks